US00PP29987P3

(12) United States Plant Patent
Tupy et al.

(10) Patent No.: US PP29,987 P3
(45) Date of Patent: Dec. 18, 2018

(54) VARIETY OF APPLE TREE NAMED 'UEB 1813'

(50) Latin Name: ***Malus domestica* (Borkh.)**
Varietal Denomination: UEB 1813

(71) Applicant: Institute of Experimental Botany AS CR, v.v.i. (UEB), Prague (CZ)

(72) Inventors: Jaroslav Tupy, Prague (CZ); Radek Cerny, Ricany u Prahy (CZ); Otto Louda, Pencin u Liberce (CZ); Jan Zima, Turnov (CZ)

(73) Assignee: Institute of Experimental Botany AS CR, v.v.i. (UEB) (CZ)

( * ) Notice: Subject to any disclaimer, the term of this patent is extended or adjusted under 35 U.S.C. 154(b) by 69 days.

(21) Appl. No.: 15/330,708

(22) Filed: Oct. 28, 2016

(65) Prior Publication Data

US 2017/0127583 P1 May 4, 2017

Related U.S. Application Data

(60) Provisional application No. 62/285,464, filed on Oct. 29, 2015.

(51) Int. Cl.
*A01H 5/08* (2018.01)

(52) U.S. Cl.
USPC ..... Plt./161

(58) Field of Classification Search
USPC ..... Plt./161
See application file for complete search history.

(56) References Cited

U.S. PATENT DOCUMENTS

PP25,671 P3 * 7/2015 Kellerhals ..... A01H 5/0875 Plt./161

* cited by examiner

*Primary Examiner* — Anne Marie Grunberg
(74) *Attorney, Agent, or Firm* — The Webb Law Firm

(57) ABSTRACT

A new and distinct dessert diploid variety of *Malus domestica* (Borkh.) that is characterized by Vf-resistance against scab, drooping tree habit, moderate vigor, and globose fruits of medium size which have a large area of red to red-purple overcolor with weakly defined stripes. The fruit flesh is firm, crisp, juicy, and with a pleasant aroma. The new variety has a late time of harvest and a medium to late time of eating maturity.

6 Drawing Sheets

Botanical classification: *Malus domestica* (Borkh.).
Varietal denomination: 'UEB 1813'.

BACKGROUND OF THE INVENTION

The present invention comprises a new and distinct cultivar of apple tree botanically classified as *Malus domestica* (Borkh.) and known by the varietal name 'UEB 1813'.

The new variety is a result of a cross in a planned breeding program between 'Topaz' (female parent, unpatented) and 'Fuji' (male parent, unpatented). The cross resulting in 'UEB 1813' occurred in the Spring of 1997 in the Czech Republic at 310 meters above sea level with a mean annual temperature of 7.7° C. and a mean annual precipitation of 680 mm. The purpose of the breeding program was to develop a late ripening, dessert apple variety with good eating qualities, attractive appearance, and with resistance against scab. The new variety was discovered in the fall of 2003 with the first fruiting of the original seedling in the Czech Republic. Subsequently, the new variety was asexually reproduced in the Czech Republic by budding/grafting on apple rootstocks in the spring of 2004.

The new variety is similar to female parent 'Topaz' in late harvesting time, in time of maturity consumption, and in having $V_f$-resistance against scab. However, 'UEB 1813' differs from its female parent in having a globose fruit shape (versus obloid in 'Topaz'), red to red-purple hue of overcolor (versus red in 'Topaz'), very large relative area of overcolor (versus medium in 'Topaz'), and drooping tree habit (versus spreading in 'Topaz'). The new variety is similar to male parent 'Fuji' in having a globose fruit shape, red to red-purple hue of overcolor, and having thin one year shoots. However, 'UEB 1813' has a late time of harvest, drooping tree habit, and exhibits $V_f$-resistance against scab, while 'Fuji' has very late time of harvest, spreading tree habit, and exhibits no $V_f$-resistance against scab.

Further, when compared to apple tree named 'UEB 38026' (concurrently applied for under separate U.S. Plant patent application Ser. No. 15/330,707), the new variety exhibits medium-sized, globose shaped fruits, while 'UEB 1813' exhibits small to medium-sized, globose-conical shaped fruits. Additionally, the fruits of 'UEB 38026' have an earlier ripening time than the fruits of 'UEB 1813'. However, both varieties have a ramified tree type with medium vigor.

The following characteristics also distinguish the new variety from other varieties known to the breeders:

- Late ripening dessert, diploid variety;
- Ramified tree type with medium vigor;
- Drooping growth habit that is easy to manage;
- Fruit size is medium;
- Fruit shape is globose;
- Fruit ground color is yellow with a red to purple-red overcolor having a pattern that is solidly flush with weakly defined stripes;
- Fruit flesh color is yellow-orange;
- Flesh is firm, crisp, and juicy, with a pleasant aroma; and
- Presence of $V_f$-resistance against scab.

The new variety has been trial and field tested and has been found to retain its distinctive characteristics and remain true to type through successive asexual propagations.

DESCRIPTION OF THE DRAWINGS

The accompanying photographic drawings illustrate the new cultivar, with the color being as nearly true as is possible with color illustrations of this type. It should be noted that colors may vary with growing conditions and with time during the year.

DESCRIPTION OF THE PLANT

Figure 1:
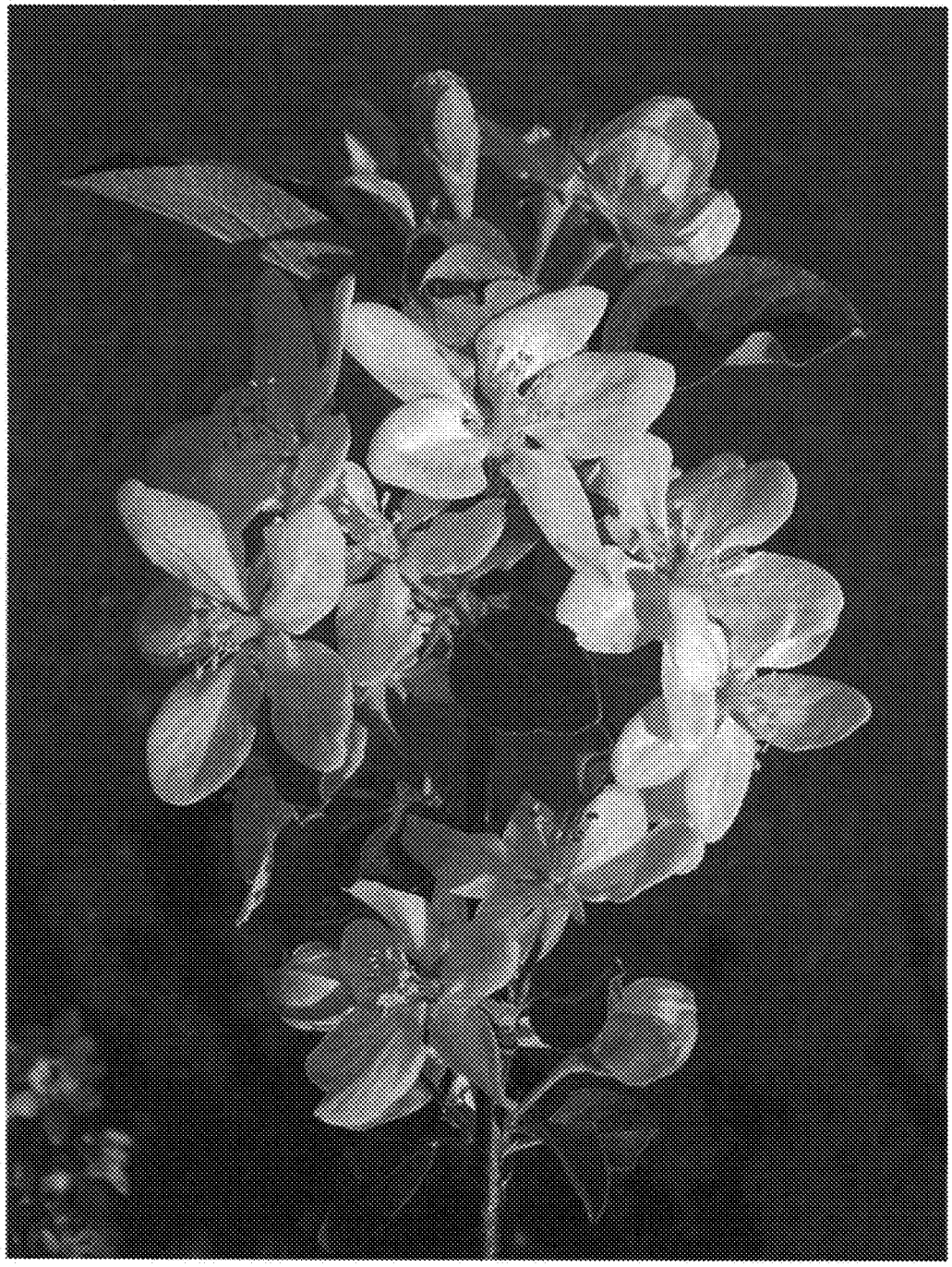
FIG. 1 illustrates a section of a tree of the new variety with opening and fully opened flowers.
Figure 2:
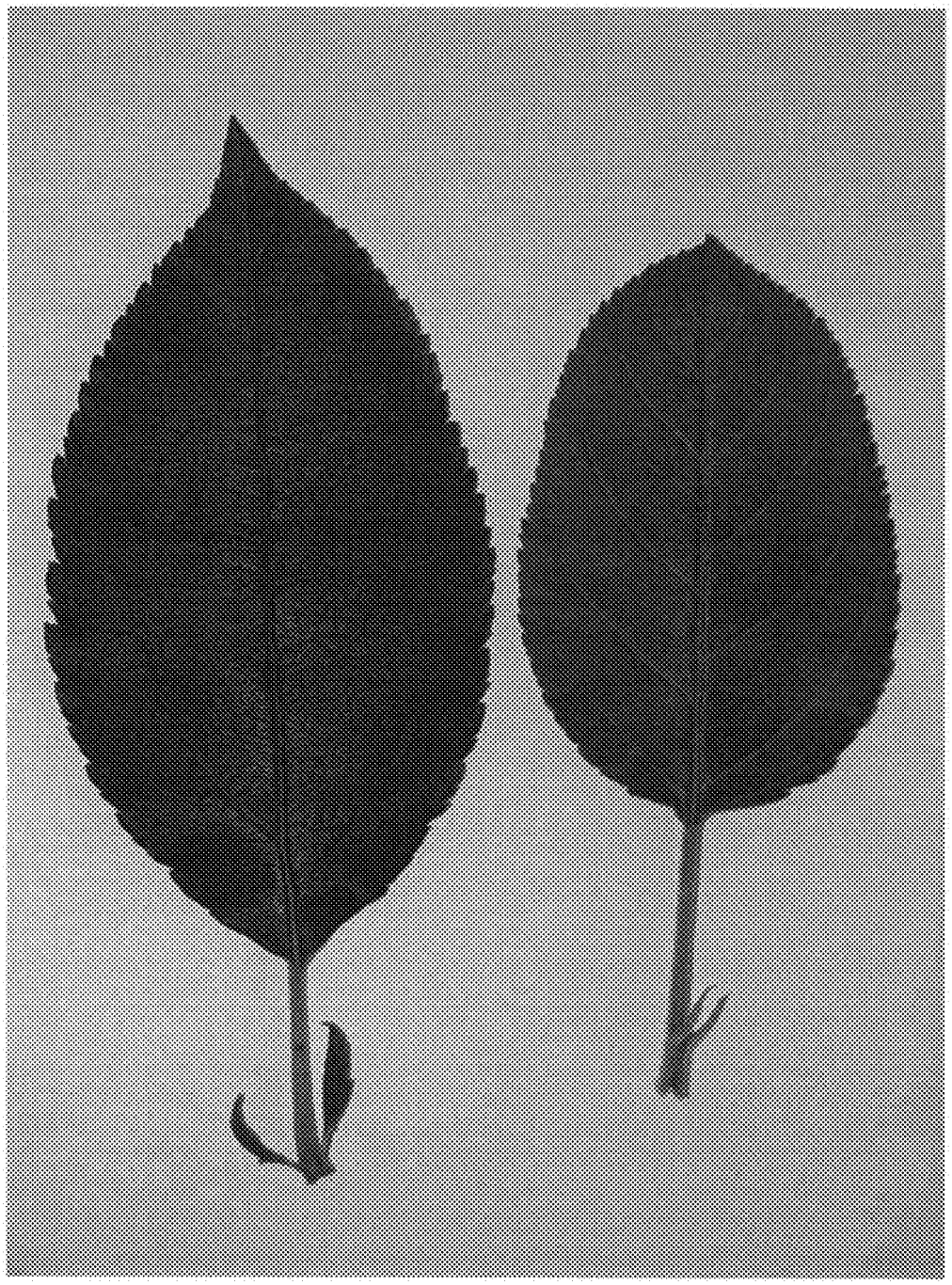
FIG. 2 illustrates a close-up view of a mature leaf and a young leaf of the new variety.
Figure 3:
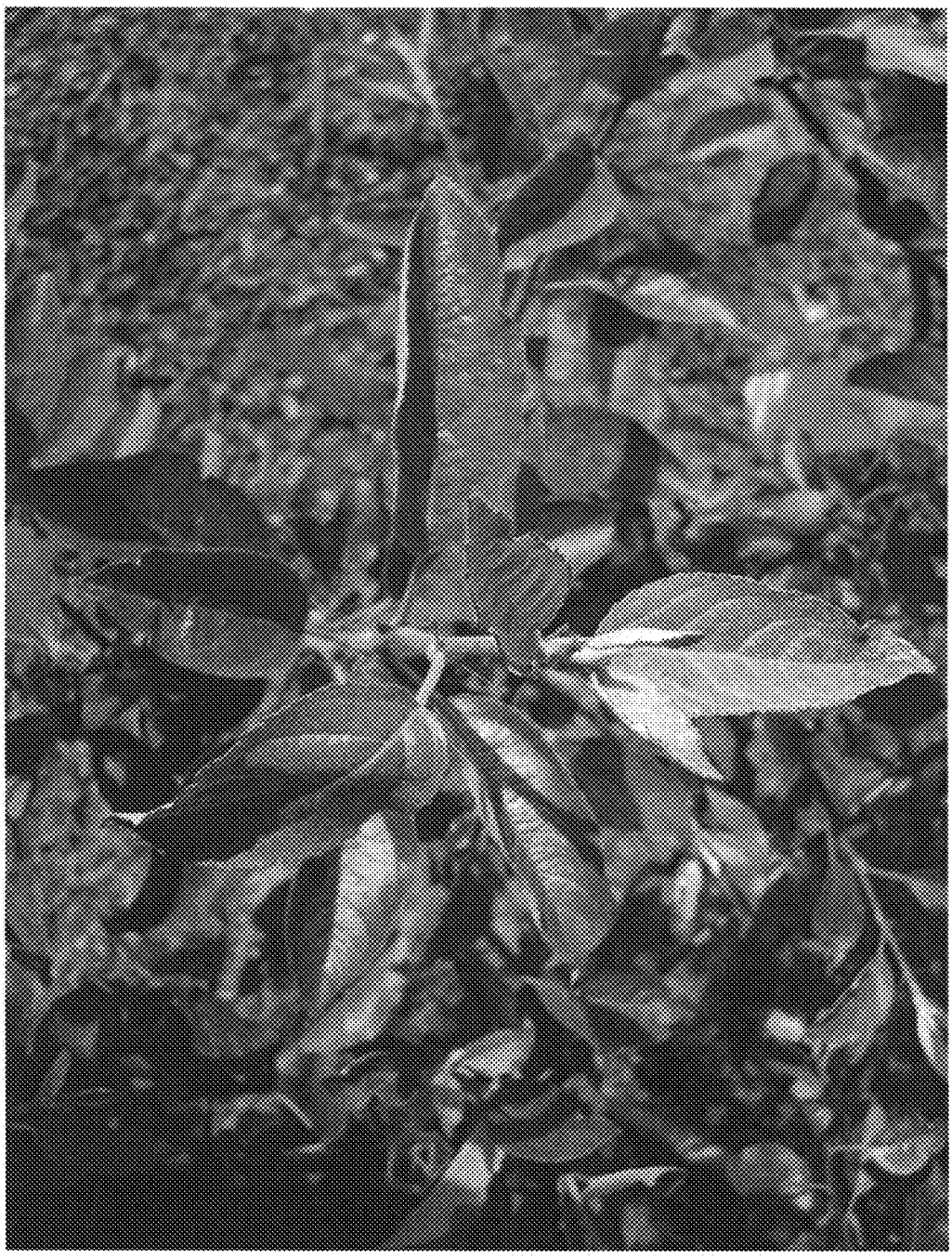
FIG. 3 illustrates a growing shoot of the new variety.
Figure 4:
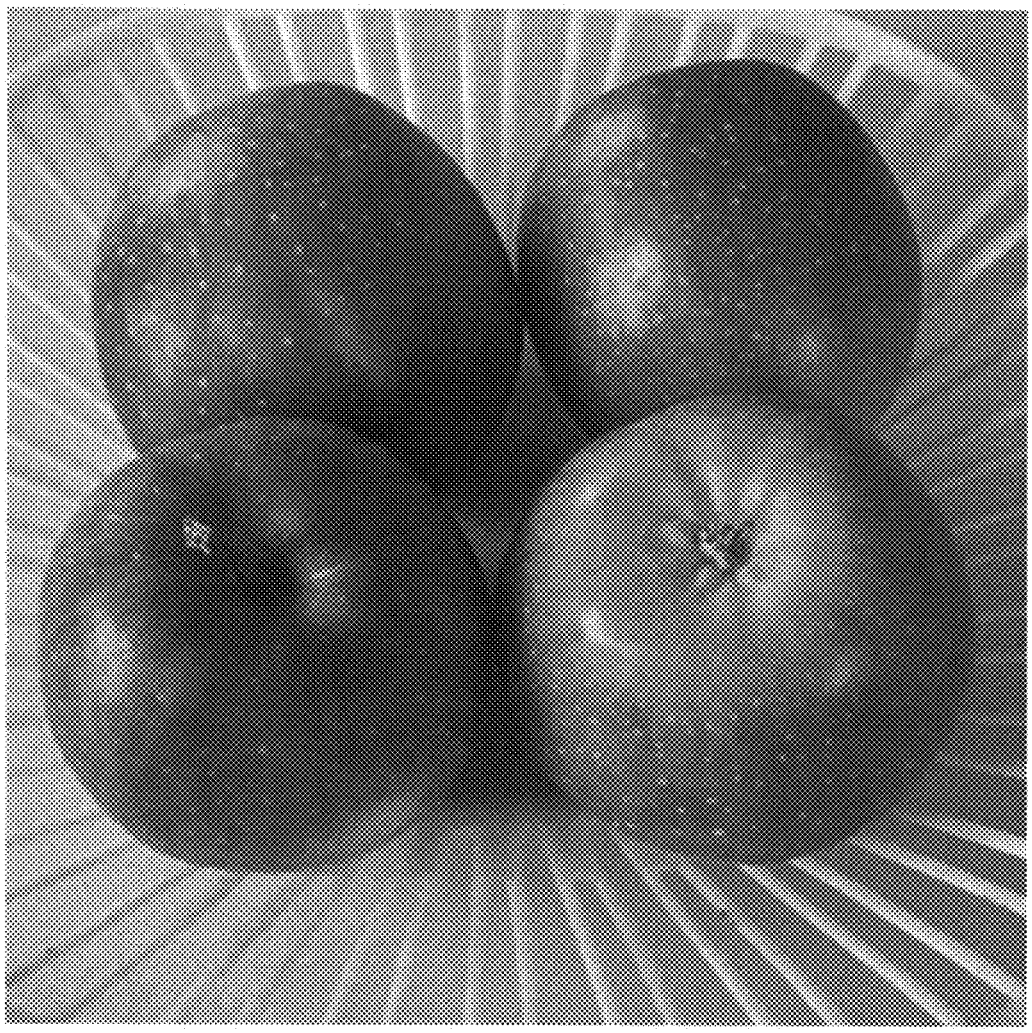
FIG. 4 illustrates a close-up view of the fruits of the new variety at picking maturity.
Figure 5:
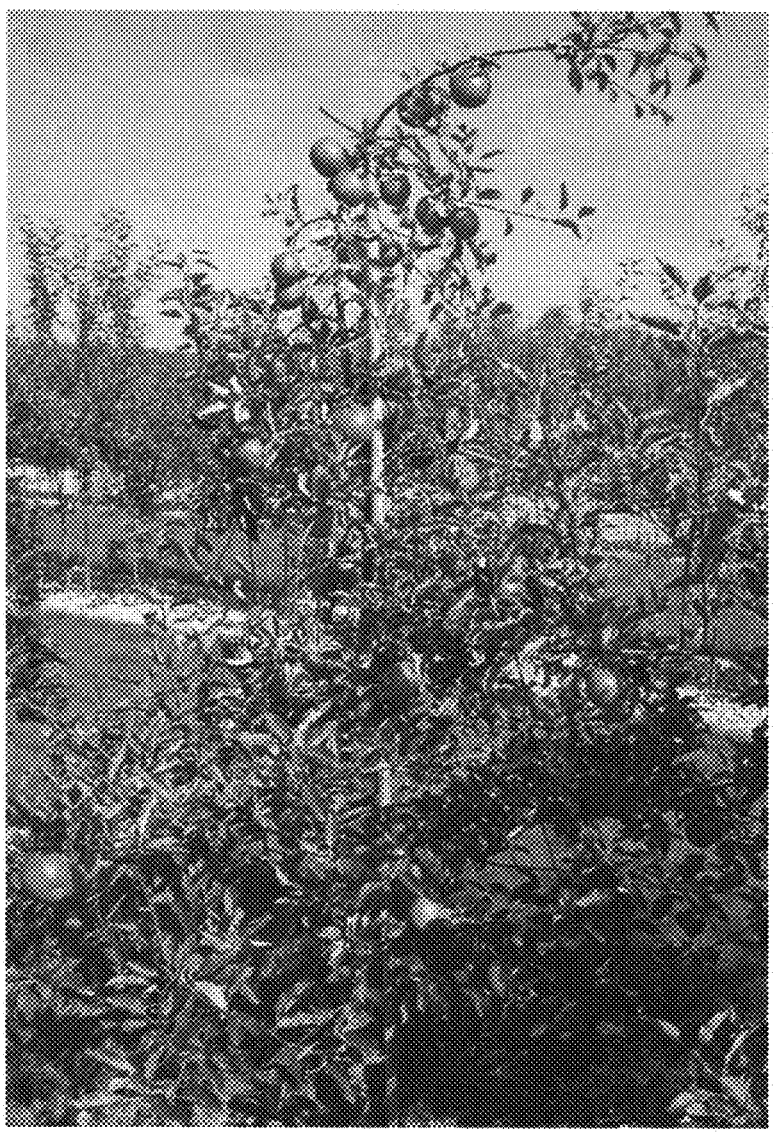
FIG. 5 illustrates a tree of the new variety grafted on the MM9 rootstock with fruits at picking maturity.
Figure 6:
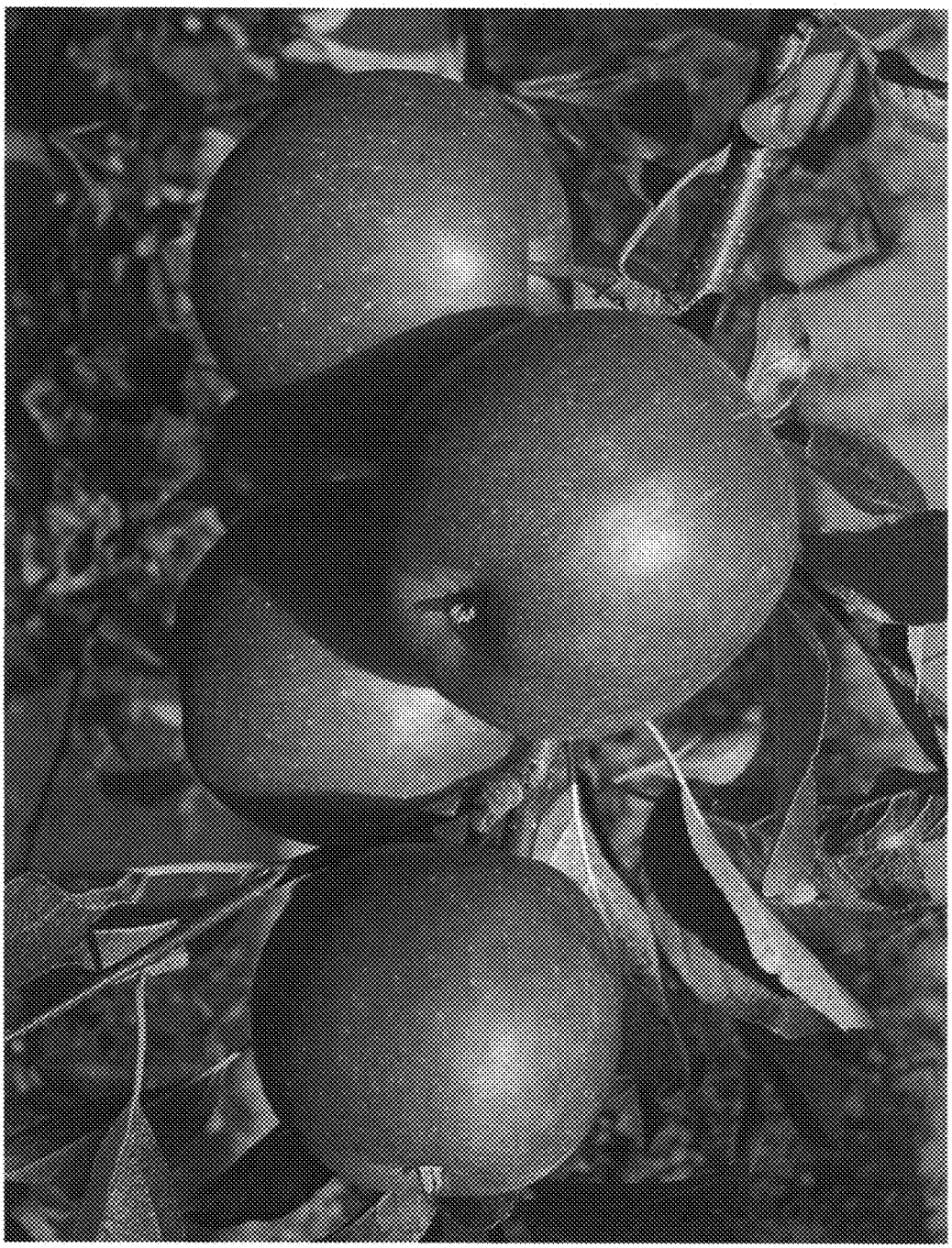
FIG. 6 illustrates details of mature fruits of the new variety.

The following detailed description sets forth characteristics of the new cultivar. The new variety was grown in natural field conditions in the Czech Republic. The following fertilizer combination was used (Kg/ha/year): 55 parts nitrogen, 25 parts phosphorous, 60 parts potassium, 55 parts calcium, and 5 parts magnesium. Color references are primarily according to The R.H.S. Colour Chart of The Royal Horticultural Society of London and were identified in natural light.

TREE

Age: 4 years after seedling grafted on MM9 rootstock.
Size: Crown height 2.5 m, width 2.8 m.
Vigor: Moderate.
Density: Medium.
Form: Rounded to pyramidal.
Production: Moderately productive.
Growth type: Ramified with a drooping habit.
Bearing: Annual, with fruit thinning
Trunk:
- *Size*.—Approximately 9.0 cm in diameter at 30.0 cm from the soil line.
- *Surface texture*.—Slightly rough.
- *Bark color*.—Greyed-Green Group RHS 197A.
- *Lenticels* (*at* 100 *cm above ground*).—Length: 1.0 mm to 5.0 mm. Width: 1.0 mm on average. Color: Greyed-Yellow Group RHS 161A to 161B. Density: Variable, 6 to 7 lenticels on average per 1 $cm^2$.

Branches:
- *Overall description*.—A conventional branching system along the tree trunk.
- *Diameter*.—Main branches on the trunk, 3.0 cm to 4.0 cm.
- *Surface texture*.—Slightly rough.
- *Color*.—Grey-Brown Group RHS 199A to RHS 199B.
- *Form*.—Moderately branching.
- *Average crotch angle*.—About 60 to 70 degrees.
- *Bud arrangement*.—Alternate with internode lengths at intervals from 2.0 cm to 4.0 cm.
- *Lenticels* (*on a* 1-*year old shoot*).—Length: Typically 1.0 mm to 4.0 mm. Width: Typically 1.0 mm. Shape: Oval. Density: Variable, with about 6 to 7 lenticels on average per 1 $cm^2$. Color: Greyed-Yellow Group RHS 161A.

Leaves (measured at the middle of growing shoot):
- *Length*.—About 71.0 mm to about 105.0 mm, averaging 88.0 mm.
- *Width*.—About 41.0 mm to about 59.0 mm, averaging about 49.0 mm.
- *Form*.—Elliptic.
- *Texture*.—Smooth.
- *Thickness*.—Medium.
- *Base*.—Symmetric, predominantly rounded.
- *Apex*.—Straightly acuminate.
- *Margin*.—Bicrenate to biserrate.
- *Attitude of leaf blade in relation to the shoot*.—Outwards.
- *Pubescence*.—Upper surface: None present. Lower surface: Very fine and weak.
- *Color*.—Young leaves: Upper surface: Yellow-Green Group RHS 144A. Lower surface: Yellow-Green Group RHS 144D. Mature leaves: Upper surface: Yellow-Green Group RHS 147A. Lower surface: Yellow-Green Group RHS 147C.
- *Petiole*.—Shape: Straight to curved, with thickening and flattening at the base. Length: About 22.0 mm to about 28.0 mm, averaging about 24.5 mm. Diameter: About 2.0 mm in the middle. Color: Yellow-Green Group RHS 146D with some Red-Purple Group RHS 59A at the base.
- *Veins*.—Venation type: Net-like, medium dense. Color: Upper surface: Yellow-Green Group RHS 146D. Lower surface: Yellow-Green Group RHS 145C.

Flower buds:
- *Pedicel*.—Length: Typically in the range of 19.0-28.0 mm, with an average of 24.0 mm. Diameter: 1.3 mm on average. Color: Predominantly Yellow-Green Group RHS 144A.
- *Bud*.—Length: 16.0 mm on average. Width: 12.0 mm on average. Color: Red-Purple Group RHS 70C.

Flowers:
- *Bloom timing*.—Medium; around May 5th — similar to 'Golden Delicious'.
- *Blooming period*.—Medium.
- *Pollination requirements*.—Diploid, self-sterile, needs pollinators.
- *Number of flowers per cluster*.—5 to 6.
- *Fragrance*.—Faint.
- *Average diameter*.—3.9 cm.
- *Petals*.—Number: 5. Length: From 21.0-26.0 mm, with an average of 23.0 mm. Width: From 13.0-17.0 mm, with an average of 15.0 mm. Shape: Ovate. Aspect: Positioned intermediate to overlapping. Margin: Entire. Texture and appearance: Soft and smooth. Color: When opening: Upper surface: White Group RHS 155D and Red-Purple Group RHS 63B. Lower surface: White Group RHS 155D and Red-Purple Group RHS 63C. Fully opened: Upper surface: White Group RHS 155D and Red-Purple Group RHS 63D. Lower surface: White Group RHS 155D and Red-Purple Group RHS 63C.
- *Sepals*.—Shape: Long-conical; pointed. Margin: Entire. Texture: Finely pubescent. Length: 8.0 mm on average. Width: 3.0 mm in the middle. Color:

Upper surface: Yellow-Green Group RHS 144B, with a Red-Purple Group RHS 59A apex. Lower surface: Yellow-Green Group RHS 145B, with a Red-Purple Group RHS 59B apex.

*Stamens*.—Number (per flower): 19 to 20. Filament length: 6.0-11.0 mm.

*Anthers*.—Shape: Oval. Length: 2.0 mm Color: Yellow Group RHS 10B.

*Pollen*.—Color: Yellow Group RHS 7B. Amount (generally): Medium.

*Pistils*.—Length: 14.0 mm on average.

*Style*.—Length: 9.0 mm on average. Color: Yellow-Green Group RHS 145B.

*Stigma*.—Shape: Rounded. Color: Yellow-Green Group RHS 151B.

Fruit:

*Bearing*.—On spurs and long shoots.

*Maturity when described*.—Full eating maturity.

*Date of picking*.—Oct. 10, 2013.

*Size*.—Axial diameter: Average of 59.0 mm. Transverse diameter: Average of 66.0 mm.

*Form*.—Globose.

*Cavity*.—Shape: Funnel. Depth: Typically between 6.0 mm and 10.0 mm, averaging 8.0 mm. Breadth: Typically between 23.0 mm and 30.0 mm, averaging 27.0 mm.

*Basin*.—Shape: Bowl-shaped, slightly ribbed. Depth: Between 5 mm and 7 mm, averaging 6 mm. Width: Between 24 mm and 30 mm, averaging 26 mm.

*Calyx*.—Persistent with long lobes, closed.

Skin:

*Thickness*.—Medium to thin.

*Texture*.—Smooth, free of russet.

*Tendency to crack*.—Absent.

*Color*.—Red Group RHS 53A to Red-Purple Group RHS 60A.

*Ground color*.—Yellow Group RHS 13B.

*Extent of young fruit anthocyanin overcolor*.—About 70% higher intensity of overcolor.

*Percentage of fruit overcolor*.—80-100%.

*Lenticels*.—Average number per fruit: 630. Average length: 0.69 mm. Average width: 0.59 mm. Color: Yellow-White Group RHS 158A.

Flesh:

*Aroma*.—Medium to strong; distinct.

*Color*.—Yellow-Orange Group RHS 18C.

*Texture*.—Fine, juicy, and crisp.

*Eating quality*.—Very good, well-balanced sugar to acid ratio.

Core:

*Bundle area*.—On longitudinal section — onion-shaped, with a height of 33.0 mm and a width of 38.0 mm.

*Aperture of the locules in the transverse section*.—Closed or slightly open.

*Bundle*.—Number of bunds is 10, with a color of Yellow-Green Group RHS 151C to RHS 151D.

*Calyx tube*.—Funnel-shaped and approximately 5.0 mm in length.

*Depth of tube to shoulder*.—11.0 mm.

*Styles*.—Persistent as dry residues.

*Stamens*.—Persistent as dry residues.

*Seed cells*.—Wall: Smooth. Depth: 8.0 mm. Breadth: 4.0 mm on cross section. Longitudinal section: About 22.0 mm (length of seed cell).

Seeds:

*Number perfect*.—Up to 17.

*Number in one cell*.—2 to 3.

*Length*.—About 7.0 mm.

*Breadth*.—About 4.0 mm.

*Form*.—Long conical with an acute tip.

*Color*.—Greyed-Orange Group RHS 166A.

Stem:

*Length*.—26.0 mm on average (typically 17.0 mm to 34.0 mm).

*Width*.—About 2.0 mm.

*Color*.—Brown Group RHS 200A to RHS 200B.

Use: As a late ripening, red colored, dessert variety with a very good eating quality.

Shipping quality: Average.

Keeping quality: Average, lasts approximately 4 months in common storage.

Tree winter hardiness: No frost damage observed at the place of origin, lowest winter temperatures approximately −20° C.

Bud winter hardiness: No frost damage observed at the place of origin, lowest winter temperatures approximately −20° C.

Drought tolerance: Unknown.

Disease resistance: $V_f$-resistance against scab.

We claim:

1. A new and distinct variety of *Malus domestica* (Borkh.) apple tree plant substantially as is herein described and illustrated.

* * * * *